US012544045B2

(12) United States Patent
Baker et al.

(10) Patent No.: US 12,544,045 B2

(45) Date of Patent: Feb. 10, 2026

(54) FLUID SAMPLE COLLECTION CONTAINER WITH CAP AND REMOVAL TOOL FOR FINGER GRIP LUER ADAPTER

(71) Applicant: Becton, Dickinson and Company, Franklin Lakes, NJ (US)

(72) Inventors: Michael Baker, Oradell, NJ (US); Daniel Feltyberger, Sparta, NJ (US); Elizabeth Stayduhar, Charlestown, MA (US); David Colie Wight, West Orange, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 509 days.

(21) Appl. No.: 18/012,403

(22) PCT Filed: Jun. 30, 2021

(86) PCT No.: PCT/US2021/039927

§ 371 (c)(1), (2) Date: Dec. 22, 2022

(87) PCT Pub. No.: WO2022/006294

PCT Pub. Date: Jan. 6, 2022

(65) Prior Publication Data

US 2023/0255604 A1 Aug. 17, 2023

Related U.S. Application Data

(60) Provisional application No. 63/047,063, filed on Jul. 1, 2020.

(51) Int. Cl.
*A61B 10/00* (2006.01)

(52) U.S. Cl.
CPC ...... *A61B 10/0045* (2013.01); *A61B 10/0096* (2013.01)

(58) Field of Classification Search
CPC ........................ A61B 10/0045; A61B 10/0096
See application file for complete search history.

(56) References Cited

U.S. PATENT DOCUMENTS 4,300,404 A * 11/1981 Mehl .................... A61B 10/007 73/863.52

5,312,009 A 5/1994 Ratajczak et al.

(Continued)

FOREIGN PATENT DOCUMENTS

CN 201417224 Y 3/2010

CN 104066384 A 9/2014

(Continued)

*Primary Examiner* — Robert J Michaud

(74) *Attorney, Agent, or Firm* — The Webb Law Firm

(57) ABSTRACT

A container assembly including a collection container and a container lid couplable to the collection container. An elongate receptacle extends from the container lid into the collection container when the container lid is coupled to the collection container. The elongate receptacle has an open end portion defined within the container lid and is configured to receive a specimen collection tube therein. A finger grip luer adapter is removably coupled to the container lid within the elongate receptacle, the finger grip luer adapter having a needle extending therefrom. An elongate cap is removably coupled to the finger grip luer adapter and is configured to extend over at least the needle of the finger grip luer adapter, wherein an upper portion of the elongate cap extends above at least a portion of the open end portion of the elongate receptacle when coupled to the finger grip luer adapter.

20 Claims, 5 Drawing Sheets

(56) References Cited

U.S. PATENT DOCUMENTS

| | | | |
|---|---|---|---|
| 5,891,099 A | 4/1999 | Nakajima et al. | |
| 6,247,592 B1 | 6/2001 | Racicot et al. | |
| 6,599,273 B1 | 7/2003 | Lopez | |
| 9,468,423 B2 | 10/2016 | Ellis | |
| 9,775,550 B2 | 10/2017 | Schaffer | |
| 9,821,124 B2 | 11/2017 | Gembrowski et al. | |
| 2006/0253103 A1 | 11/2006 | Utterberg et al. | |
| 2009/0069783 A1 | 3/2009 | Ellstrom et al. | |
| 2011/0094319 A1 | 4/2011 | Yong | |
| 2013/0133132 A1* | 5/2013 | Chiarin | A47K 11/12<br>4/479 |
| 2013/0175266 A1 | 7/2013 | Ellis | |

FOREIGN PATENT DOCUMENTS

| | | | |
|---|---|---|---|
| JP | S5664639 | A | 6/1981 |
| JP | H03504808 | A | 10/1991 |
| JP | H10272181 | A | 10/1998 |
| WO | 2011073729 | A1 | 6/2011 |

* cited by examiner

FLUID SAMPLE COLLECTION CONTAINER WITH CAP AND REMOVAL TOOL FOR FINGER GRIP LUER ADAPTER

CROSS-REFERENCE TO RELATED APPLICATIONS

This application is the United States national phase of International Application No. PCT/US2021/039927 filed Jun. 30, 2021, and claims priority to U.S. Provisional Application Ser. No. 63/047,063, entitled "Fluid Sample Collection Container with Cap and Removal Tool for Finger Grip Luer Adapter", filed Jul. 1, 2020, the entire disclosures of which are hereby incorporated by reference in their entirety.

BACKGROUND

Field of the Disclosure

The present disclosure relates generally to a container assembly for collecting a fluid specimen. More particularly, the present disclosure relates to a container assembly including a combined finger grip luer adapter (FGLA) cap and removal tool.

Description of the Related Art

To conduct laboratory testing on biological fluid samples such as urine, it is necessary to provide a container for collecting the fluid sample. These collection containers typically include a cup-shaped container with a removable lid. Once a fluid sample has been collected in the container, the lid is reapplied. The collection container may then be transported to a laboratory or other testing facility where a sample of the collected specimen is extracted for test purposes.

To simplify the sample extraction process, prior collection containers have used lids which not only cover and seal the collection container, but also provide for the use of an extraction device which permits the extraction of a sample of the fluid specimen. Such lids may include a receptable or cavity which supports a tube extending within the cavity to the lower end of the cup-shaped container in fluid communication with the specimen contained within the container. The tube or the lid may include an elongated receptacle housing a cannula and needle so that an air-evacuated collection device (e.g., a specimen collection tube) may be attached thereto to draw a portion of the collected sample thereinto without the need for removal of the lid. In such configurations, the sample can be removed without spilling or contaminating the sample and/or cavity area. Subsequent samples may be drawn from the collection container by using a plurality of collection tubes.

However, in prior collection containers, the cannula is provided within the elongated receptacle in the form of a finger grip luer adapter (FGLA) that is non-removably integrated into the container lid. Thus, when the user has completed all sample collection(s) and wishes to dispose of the container assembly, the entire removable lid must be disposed of in an appropriate sharps container or sharps biohazard container. Due to their large volume, removable lids will quickly fill the sharps container, necessitating frequent service by a qualified disposal firm to safely handle the sharps and/or biohazard waste. As such disposal services are far more expensive than conventional waste disposal services, health care providers generally seek to minimize the accumulated volume of sharps and/or biohazard waste.

Additionally, due to the FGLA being integrated into the lid, the patient and/or healthcare worker may be more at risk of needle-stick injuries during sample collection, transport, and/or disposal.

SUMMARY

In view of the foregoing, there exists a need for a fluid sample collection container having a reduced volume of sharps waste and which protects users and/or healthcare workers from potential needle-stick injuries.

In accordance with an embodiment of the present invention, a container assembly for collecting a fluid specimen includes a collection container defining a chamber for receiving the fluid specimen, and a container lid couplable to an open end of the collection container to at least partially close the open end thereof. The container assembly also includes an elongate receptacle extending from the container lid into the chamber of the collection container when the container lid is coupled to the open end of the collection container, the elongate receptacle having an open end portion defined within the container lid and configured to receive a specimen collection tube therein. The container assembly also includes a finger grip luer adapter removably coupled to the container lid within the elongate receptacle, with the finger grip luer adapter including a needle extending therefrom. The container assembly further includes an elongate cap removably coupled to the finger grip luer adapter and configured to extend over at least the needle of the finger grip luer adapter, wherein an upper portion of the elongate cap extends above at least a portion of the open end portion of the elongate receptacle when coupled to the finger grip luer adapter.

In certain configurations, the upper portion of the elongate cap include a finger grip portion, and the finger grip portion is configured to extend above an upper surface of the container lid when coupled to the finger grip luer adapter. The finger grip portion may include a ribbed or textured surface so as to improve a user's grip on the finger grip portion of the elongate cap. The elongate cap may include an elongate portion and a cavity, wherein the cavity extends from an open end on a distal end of the elongated portion. The distal end of the elongated portion of the elongate cap may be configured to slip-fittingly or press-fittingly couple to an upper portion of the finger grip luer adapter.

In certain embodiments, the upper portion of the finger grip luer adapter includes a ribbed or textured surface. In other configurations, the lower portion of the finger grip luer adapter is configured to be removably couplable to the elongate receptacle of the container lid. The lower portion of the finger grip luer adapter may include external threads, and the external threads may be configured to mate with a corresponding internal thread portion of the elongate receptacle. The finger grip luer adapter may be threadingly coupled to the container lid.

In other configurations, the finger grip luer adapter is removable from the container lid by way of counterclockwise rotation of the elongate cap when the elongate cap is coupled to the finger grip luer adapter. At least one of the collection container and the container lid are formed of a polymeric resin. Optionally, the elongate cap is formed of a polymeric resin.

In accordance with a further embodiment of the present invention, a container lid assembly for use with a container assembly for collecting a fluid specimen, includes an elongate receptacle having an open end portion defined within the container lid and configured to receive a specimen collection tuber therein. The container lid assembly also includes a finger grip luer adapter removably coupled to the container lid within the elongate receptacle, the finger grip luer adapter comprising a needle extending therefrom, and an elongate cap removably coupled to the finger grip luer adapter. The elongate cap is configured to extend over at least the needle of the finger grip luer adapter, in which an upper portion of the elongate cap extends above at least a portion of the open end portion of the elongate receptacle when coupled to the finger grip luer adapter.

In certain configurations, the distal end of the elongate cap is configured to slip-fittingly or press-fittingly couple to an upper portion of the finger grip luer adapter. The upper portion of the finger grip luer adapter may include a ribbed or textured surface. The lower portion of the finger grip luer adapter may be configured to be removably couplable to the elongate receptacle of the container lid. Optionally, the lower portion of the finger grip luer adapter may include external threads, which are configured to mate with a corresponding internal thread portion of the elongate receptacle. The finger grip luer adapter may be removable from the container lid by way of counterclockwise rotation of the elongate cap when the elongate cap is coupled to the finger grip luer adapter.

In accordance with yet another embodiment of the present invention, a method of forming a container assembly for collecting a fluid specimen includes providing a collection container defining a chamber for receiving the fluid specimen. The method also includes providing a container lid couplable to the collection container, wherein the container lid comprises an elongate receptacle having an open end portion defined within the container lid and configured to receive a specimen collection tube therein. The method also includes coupling a finger grip luer adapter to the container lid within the elongate receptacle, the finger grip luer adapter having a needle extending therefrom. The method further includes coupling an elongate cap to the finger grip luer adapter such that the elongate cap extends over at least the needle of the finger grip luer adapter, wherein an upper portion of the elongate cap extends above at least a portion of the open end portion of the elongate receptacle when coupled to the finger grip luer adapter.

In certain configurations, the method further requires that the finger grip luer adapter is threadingly coupled to the elongate receptacle of the container lid.

Further details and advantages of the present disclosure will be understood from the following detailed description read in conjunction with the accompanying drawings.

DESCRIPTION OF THE INVENTION

Figure 1:
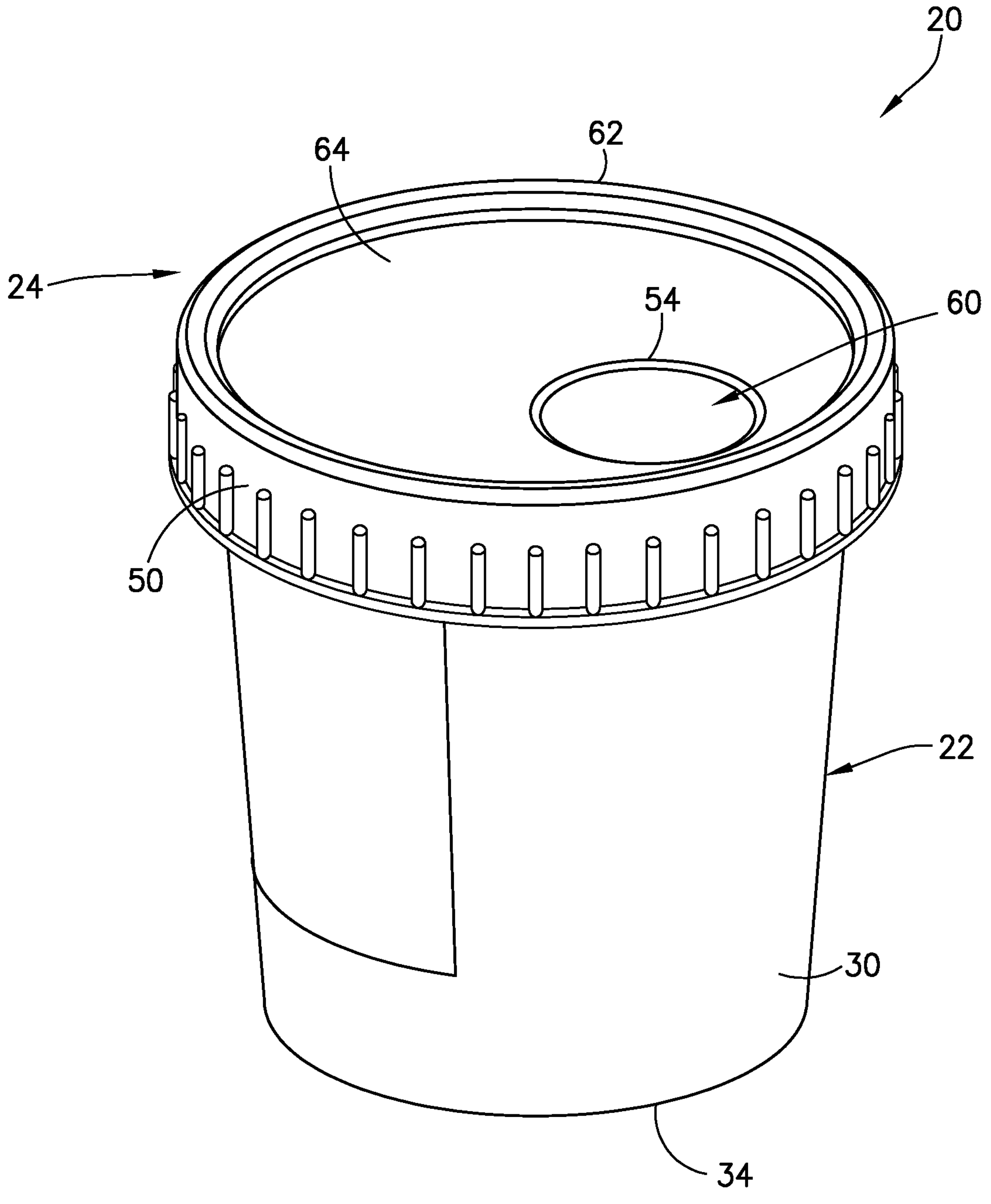
FIG. 1 is a perspective view of a fluid sample collection container assembly in accordance with an aspect of the present disclosure.

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For the purposes of the description hereinafter, the terms “upper”, “lower”, “right”, “left”, “vertical”, “horizontal”, “top”, “bottom”, “lateral”, “longitudinal”, and derivatives thereof shall relate to the invention as it is oriented in the drawings. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting.

Referring to FIG. 1, a fluid sample collection container assembly 20 in accordance with an aspect of the present disclosure is shown. Fluid sample collection container assembly 20 includes a collection container 22 and a container lid 24. An exemplary collection container assembly 20 in accordance with the present disclosure may be used to safely collect a fluid specimen (e.g., urine), transport the fluid specimen, and draw a sample of the fluid specimen.

In one embodiment, collection container 22 and container lid 24 may be formed from any conventional material such as, e.g., a polymeric resin. Polymeric resins are well known in the art and include, for example, polyethylene, polycarbonate, polystyrene, and similar polymeric resinous materials. However, it is to be understood that collection container 22 and/or container lid 24 may be formed of other appropriate materials, and may be formed of different materials.

Collection container 22 generally includes a sidewall 30 extending between a first, open end (not shown) and a second, closed end 34. Sidewall 30 defines an interior chamber for receiving a fluid specimen such as, e.g., urine. In one embodiment, sidewall 30 of collection container 22 comprises a slightly tapering, tubular vessel having continuous, tapered sidewalls 30. In one embodiment, the collection chamber of container 22 is suitable for holding biologically hazardous materials. In one embodiment, sidewall 30 of collection container 22 may include at least one fill level indicator which identifies a fluid level of a collected fluid specimen.

Figure 2:
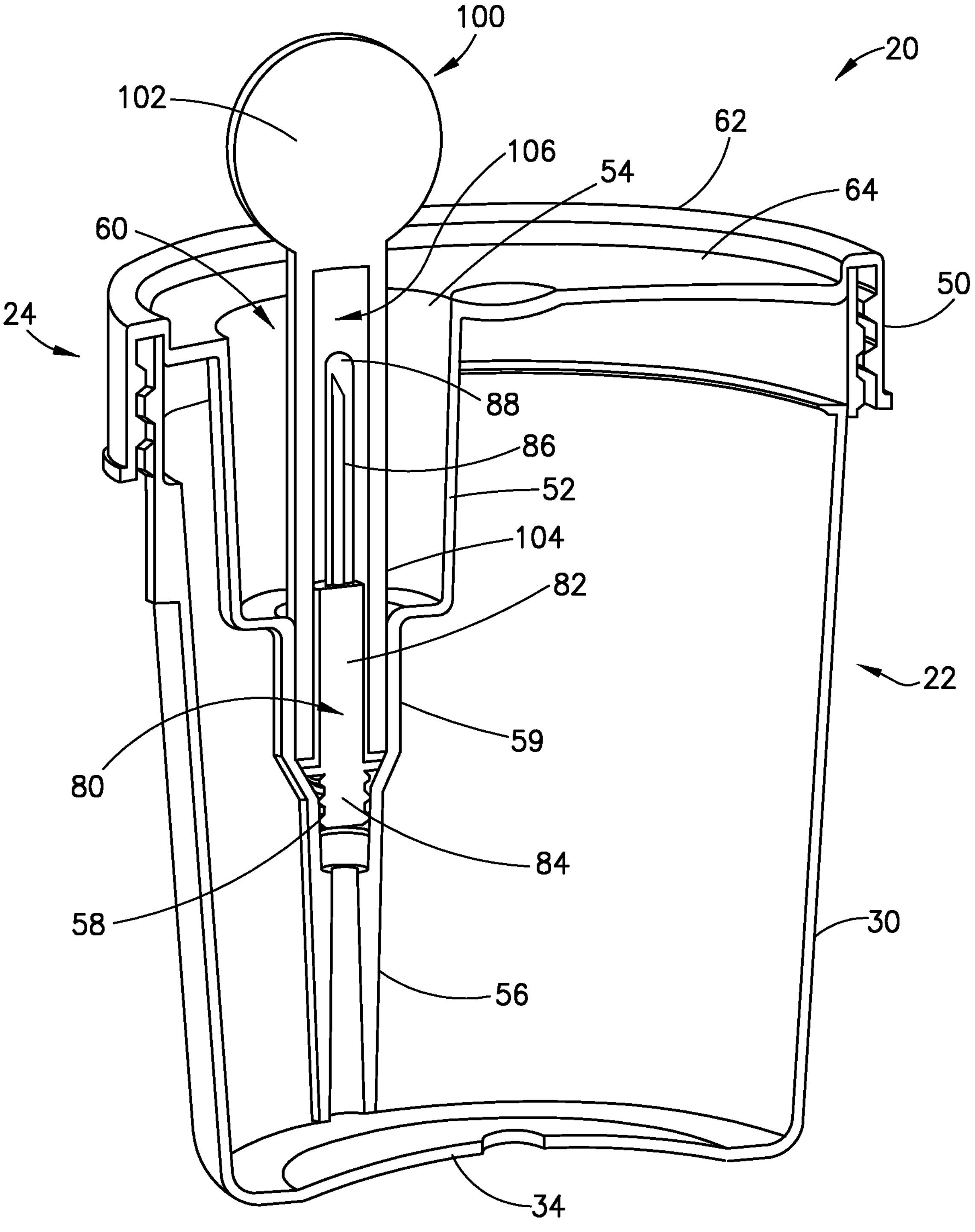
FIG. 2 is a cross-sectional view of the fluid sample collection container assembly having a FGLA cap and removal tool in accordance with an aspect of the present disclosure.

Container lid 24 generally includes a flange 50 extending around its outer rim, with flange 50 being sized to provide a tight fit upon the collection container 22 when container lid 24 is placed over the first, open end of collection container 22. In one embodiment, container lid 24 includes a generally disc-shaped component having an outer or peripheral zone 62 and an inner or central zone 64. Flange 50 extends downward from peripheral zone 62 of container lid 24. As is shown in FIG. 2, flange 50 includes an inner surface which includes a means or mechanism for sealingly engaging container lid 24 with the collection container 22. In one embodiment, flange 50 includes an interior threaded portion, thereby enabling container lid 24 to be threadingly connectable to a corresponding exterior threaded portion of the collection container 22. In other embodiments, the sealing portion of container lid 24 may include a snap fit mechanism, a ball detent, an interference fit mechanism, locking tabs, a spring loaded locking mechanism, a latch, or other similar mechanism to sealingly engage container lid 24 to collection container 22, thereby substantially preventing a fluid specimen contained within collection container 22 and container lid 24 from leaking out, while also preventing contaminants from entering.

Referring to FIG. 2, container lid 24 also includes an elongate receptacle 52 extending from the central zone 64 into collection container 22 and towards the second, closed end 34 of collection container 22. Receptacle 52 includes an open end portion 54 and an opposing lower end portion 56, with a receiving cavity 60 defined therein. In one embodiment, receiving cavity 60 is sized and shaped to receive a specimen collection tube such as, e.g., an evacuated tube (not shown). In this way, a fluid specimen within collection container 22 can be transferred to the specimen collection tube without the need to remove container lid 24.

Referring still to FIG. 2, a finger grip luer adapter (FGLA) 80 is positioned within a central portion 59 of the receptacle 52. Specifically, FGLA 80 includes an upper portion 82 and a lower portion 84. Upper portion 82 is configured to extend upward toward receiving cavity 60 and may include ribbed or textured outer sidewalls. On the other hand, in one embodiment, lower portion 84 includes external threads, which are configured to mate with a corresponding internal thread portion 58 of the receptacle 52. In this way, the FGLA 80 may be removably secured to the receptacle 52 via a threaded interface. Alternatively, in another embodiment, FGLA 80 may be removably secured to receptacle 52 by way of a press-fit or slip-fit connection.

Additionally, FGLA 80 includes a needle 86 extending upward from upper portion 82 and into the receiving cavity 60. In one embodiment, a retractable sleeve 88 may extend over needle 86. While not shown, needle 86 is configured to pierce the stopper of a specimen collection tube that is inserted into receptacle 52 by a user. In this way, a fluid specimen may be drawn from the collection container 22 into the specimen collection tube through the lower end portion 56 of receptacle 52 and FGLA 80, thereby enabling the user to collect the fluid specimen without necessitating removal of the container lid 24 from collection container 22.

FIG. 2 further shows a combined FGLA cap and removal tool 100 in accordance with an aspect of the present disclosure. As will be described in detail hereinbelow, FGLA cap and removal tool 100 serves the dual purpose of protecting all users from needle-stick injuries and substantially reducing sharps waste when the fluid sample collection container assembly 20 is to be discarded.

In one embodiment, FGLA cap and removal tool 100 includes a finger grip portion 102. Finger grip portion 102 is configured to extend outside of the receiving cavity 60 and above the central zone 64 of container lid 24 to allow for easy access by the user. Additionally, in one embodiment, the finger grip portion 102 may be ribbed, textured, or otherwise treated so as to improve the user's hold on the finger grip portion 102. The FGLA cap and removal tool 100 may be formed of any appropriate material or materials such as, e.g., a polymeric resin. Examples of polymeric resins include, e.g., polyethylene, polycarbonate, polystyrene, and similar polymeric resinous materials. However, it is to be understood that FGLA cap and removal tool 100 may be formed of other appropriate materials, and may be formed of two or more different materials.

FGLA cap and removal tool 100 also includes an elongated bottom portion 104. A distal end of the elongated portion 104 is open, and a cavity 106 is formed within the elongated portion 104. The cavity 106 extends from the open end of elongated portion 104 toward the finger grip portion 102. As is shown in FIG. 2, a lower section of cavity 106 of elongated portion 104 is configured to be slip-fit or press-fit over the upper portion 82 of FGLA 80 such that the elongated portion 104 is removably secured to upper portion 82 of FGLA 80. As disclosed above, the upper portion 82 may include ribbed or textured outer sidewalls, which may aid in providing a secure interface between the FGLA 80 and the FGLA cap and removal tool 100. Additionally and/or alternatively, the inner sidewall of elongated portion 104 may also be ribbed or textured. Furthermore, in another embodiment, the lower section of cavity 106 of elongated portion 104 may include a threaded portion configured to mate with a complimentary threaded portion on the upper portion 82 of the FGLA 80.

As is shown in FIG. 2, the cavity 106 is sized so as extend over the needle 86 of FGLA 80. In this way, when FGLA cap and removal tool 100 is in position on FGLA 80, the FGLA cap and removal tool 100 acts to protect all users (e.g., patients and healthcare workers) from potential needle stick injuries, as needle 86 is completely enclosed within cavity 106. As the FGLA cap and removal tool 100 is slip-fit or press-fit onto FGLA 80, the user can remove the FGLA cap and removal tool 100 by applying an upward pulling force via the finger grip portion 102. Conversely, the user can replace the FGLA cap and removal tool 100 over the FGLA 80 by applying a downward pushing force via the finger grip portion 102.

However, while FGLA cap and removal tool 100 may be slid onto (or removed from) FGLA 80 via axial force relative to the FGLA 80, the interface between lower section of cavity 106 of elongated portion 104 and the upper portion 82 of FGLA 80 is sufficiently constricted so as to transfer rotational force applied by the user via finger grip portion 102 onto the FGLA 80. That is, if the user rotates the FGLA cap and removal tool 100 in a counterclockwise direction, lower portion 84 of FGLA 80 will unthread from internal thread portion 58 of receptacle 52. As the user continues to rotate the FGLA cap and removal tool 100, the FGLA 80 will eventually disconnect entirely from receptacle 52, leaving the FGLA 80 secured to only the FGLA cap and removal tool 100. In this way, the FGLA 80 (and the incorporated needle 86) are separable from the container lid 24, with the needle 86 being enclosed within the elongated bottom portion 104 of FGLA cap and removal tool 100.

Once removed, the user may then dispose of both the FGLA cap and removal tool 100 and the attached FGLA 80 in an appropriate sharps container or sharps biohazard container. As discussed above, conventional container lids typically used in specimen extraction via evacuated tubes include a finger grip luer adapter (FGLA) that is non-removably integrated into the container lid. Thus, the entire lid assembly must be disposed of within a sharps container or sharps biohazard container. However, in accordance with embodiments of the present disclosure, only the FGLA cap and removal tool 100 and removable FGLA 80 need be disposed of in a sharps container or sharps biohazard container, thereby greatly reducing the volume (and subsequent cost) of sharps waste, as the container lid 24 and collection container 22 may be disposed of separately as standard medical waste.

Figure 3B:
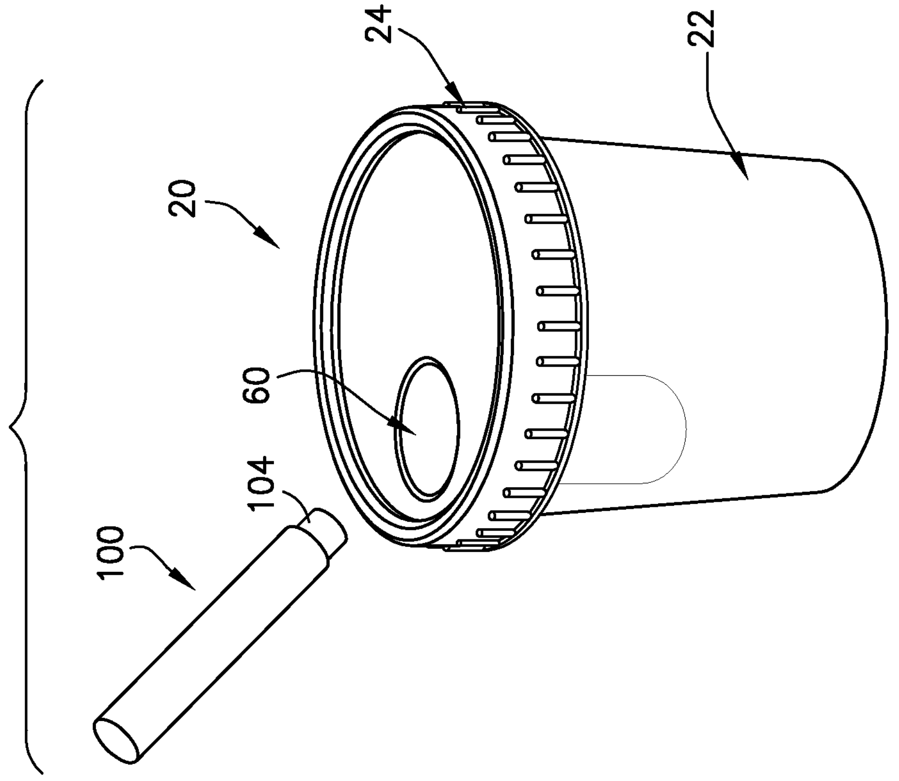
FIG. 3B is a perspective view of the fluid sample collection container assembly and FGLA cap and removal tool in a second use configuration.
Figure 3A:
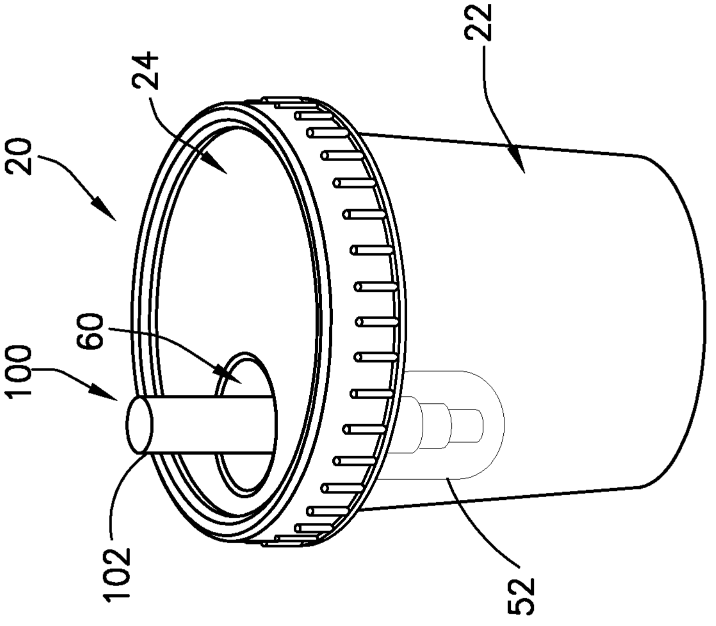
FIG. 3A is a perspective view of the fluid sample collection container assembly and FGLA cap and removal tool in a first use configuration.

Referring to FIGS. 3A-3D, various in-use views of fluid sample collection container assembly 20 in accordance the present disclosure are shown. FIG. 3A illustrates fluid sample collection container assembly 20 prior to or after fluid sample collection, wherein FGLA cap and removal tool 100 is positioned on the needle and FGLA (not shown). In this way, the FGLA cap and removal tool 100 protects all users from the needle housed within the receiving cavity 60 of container lid 24.

Referring to FIG. 3B, when the user wishes to the expose the needle and FGLA within receiving cavity 60 in order to collect a fluid sample via, e.g., an evacuated tube, the FGLA cap and removal tool 100 may be pulled upward, thereby releasing the slip-fit or press-fit connection between the FGLA and the elongated portion 104. After collection of the fluid sample, the FGLA cap and removal tool 100 may be returned to the position shown in FIG. 3A.

Figure 3C:
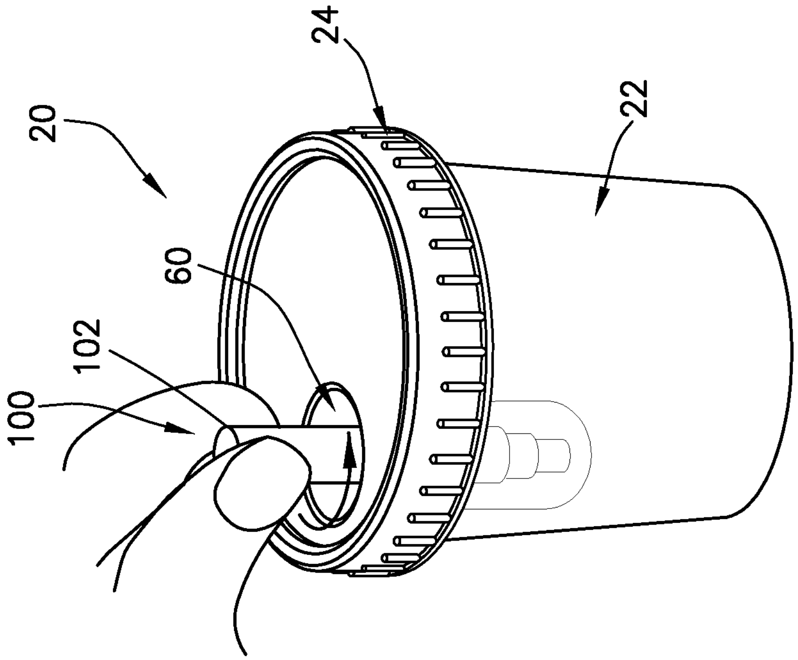
FIG. 3C is a perspective view of the fluid sample collection container assembly and FGLA cap and removal tool in a third use configuration.
Figure 3D:
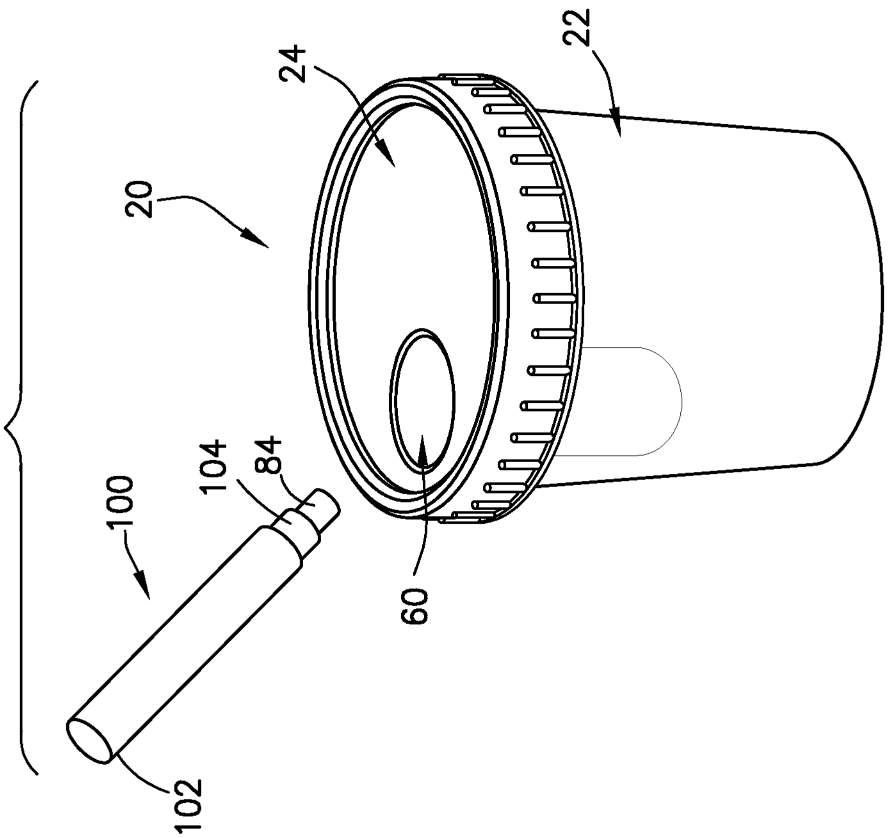
FIG. 3D is a perspective view of the fluid sample collection container assembly and FGLA cap and removal tool in a fourth use configuration.

When all necessary fluid sample(s) have been collected from the collection container 22 and the user wishes to discard of the fluid sample collection container assembly 20, the user may rotate the FGLA cap and removal tool 100 in a counter-clockwise direction, as is shown in FIG. 3C. As described above, such rotation allows for the separation of the FGLA from the container lid 24, with the needle of the FGLA still being protected within the elongated portion 104 of the FGLA cap and removal tool 100, as is shown in FIG. 3D. The user may then discard of the combined FGLA cap and removal tool 100 and FGLA into an appropriate sharps container or sharps biohazard container, while the remaining portions of the fluid sample collection container assembly 20 (i.e., the collection container 22 and the container lid 24) may be disposed of in a standard medical waste container.

Figure 4:
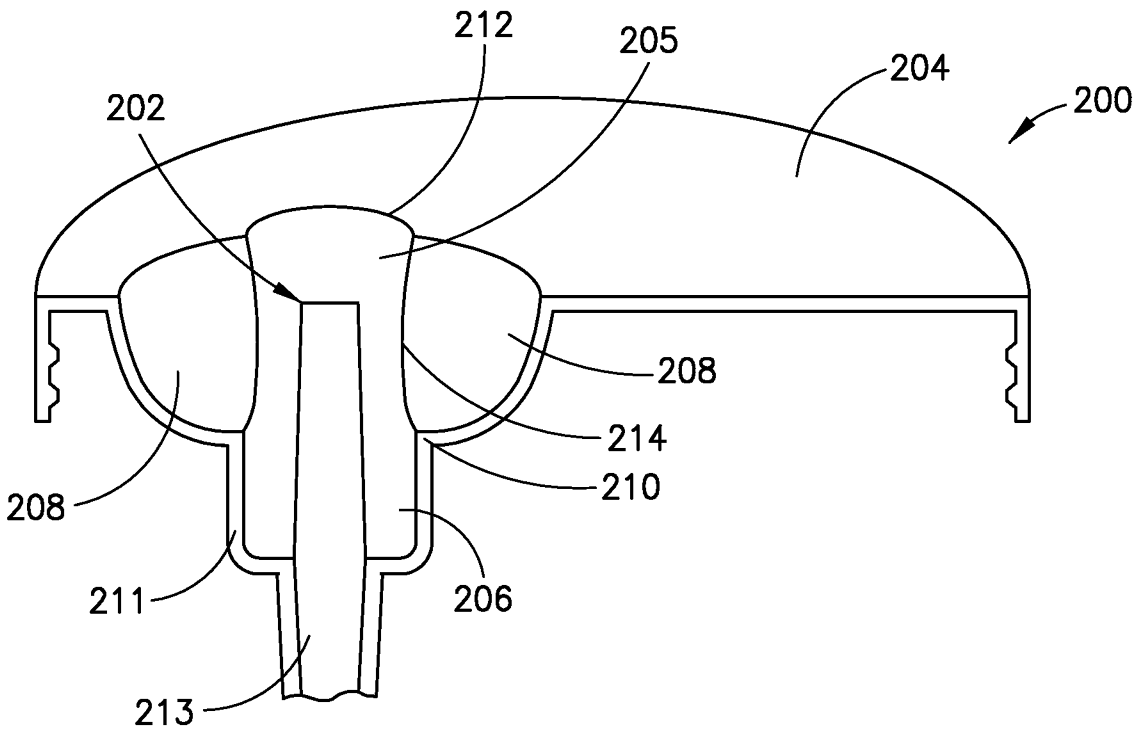
FIG. 4 is a cross-sectional perspective view of a container lid assembly for use with a fluid sample collection container assembly, FGLA cap and removal tool in accordance with another aspect of the disclosure.

Next, referring to FIG. 4, a container lid assembly 200 for use with a fluid sample collection container assembly in accordance with another aspect of the present disclosure is shown. In the embodiments described above with respect to FIGS. 2-3D, the fluid sample collection container assembly 20 included an FGLA cap and removal tool 100 that at least partially extends above a top surface 64 of the container lid 24, thereby enabling the user to grip the FGLA cap and removal tool 100 without reaching into the receiving cavity 60. However, in the embodiment shown in FIG. 4, container lid assembly 200 includes a FGLA cap and removal tool 202, the uppermost point of which extends below a top surface 204 of the container lid assembly 200.

Referring still to FIG. 4, the container lid assembly 200 includes an elongate receptacle 211, which is configured to extend into a collection container (not shown). An opening 212 is formed in the top surface 204 of the container lid assembly 200 above the elongate receptacle 211, while a lower portion 213 extends below the elongate receptacle 211. While not shown in FIG. 4, is to be understood that the lower portion 213 may be configured to receive a finger grip luer adapter (FGLA), similar to FGLA 80 shown and described with respect to FIG. 2, with the FGLA cap and removal tool 202 configured to extend over portions of the FGLA to protect from needle stick injuries and/or enable removal of the FGLA without needle exposure.

Elongate receptacle 211 includes cut-out portions 208 at an upper end portion thereof, with the cut-out portions 208 defining an open end portion 214 accessible to the fingers of the user. When installed, an upper portion of the FGLA cap and removal tool 202 extends within an upper receiving cavity 205 and above at least a portion of the open end portion 214, while a lower portion of the FGLA cap and removal tool 202 extends within a lower receiving cavity 206, which lies below the open end portion 214. The upper receiving cavity 205 is defined between the opening 212 and a juncture 210 of the elongate receptacle 211, while the lower receiving cavity 206 is defined between the juncture 210 and the lower surface of the elongate receptacle 211. When combined, the upper receiving cavity 205 and lower receiving cavity 206 are sized and shaped to receive a specimen collection tube such as, e.g., an evacuated tube (not shown). In this way, a fluid specimen within the collection container can be transferred to the specimen collection tube without the need to remove container lid assembly 200.

Due to the cut-out portions 208 formed in the container lid assembly 200, the FGLA cap and removal tool 202 need not include a gripping portion which extends above the top surface 204 in order for a user to access the FGLA cap and removal tool 202. However, because the needle of the FGLA is housed within the lower receiving cavity 206 of the elongate receptacle 211, the user is substantially protected from needle stick injuries when installing or removing the FGLA cap and removal tool 202.

While several embodiments of a fluid sample collection container assembly are shown in the accompanying figures and described hereinabove in detail, other embodiments will be apparent to, and readily made by, those skilled in the art without departing from the scope and spirit of the invention. For example, it is to be understood that this disclosure contemplates, to the extent possible, that one or more features of any embodiment can be combined with one or more features of any other embodiment. Accordingly, the foregoing description is intended to be illustrative rather than restrictive.

What is claimed is:

1. A container assembly for collecting a fluid specimen, comprising:

a collection container defining a chamber for receiving the fluid specimen; and a container lid couplable to an open end of the collection container to at least partially close the open end thereof, an elongate receptacle extending from the container lid into the chamber of the collection container when the container lid is coupled to the open end of the collection container, the elongate receptacle having an open end portion defined within the container lid and configured to receive a specimen collection tube therein;

a finger grip luer adapter removably coupled to the container lid within the elongate receptacle, the finger grip luer adapter comprising a needle extending therefrom; and an elongate cap removably coupled to the finger grip luer adapter and configured to extend over at least the needle of the finger grip luer adapter, wherein an upper portion of the elongate cap extends above at least a portion of the open end portion of the elongate receptacle when coupled to the finger grip luer adapter;

wherein the finger grip luer adapter is removable from the elongate receptacle through the open end portion of the elongate receptacle.

2. The container assembly of claim 1, wherein the upper portion of the elongate cap comprises a finger grip portion, and wherein the finger grip portion is configured to extend above an upper surface of the container lid when coupled to the finger grip luer adapter.

3. The container assembly of claim 2, wherein the finger grip portion comprises a ribbed or textured surface so as to improve a user's grip on the finger grip portion of the elongate cap.

4. The container assembly of claim 1, wherein the elongate cap comprises an elongated portion and a cavity, wherein the cavity extends from an open end on a distal end of the elongated portion.

5. The container assembly of claim 4, wherein the distal end of the elongated portion of the elongate cap is configured to slip-fittingly or press-fittingly couple to an upper portion of the finger grip luer adapter.

6. The container assembly of claim 5, wherein the upper portion of the finger grip luer adapter comprises a ribbed or textured surface.

7. The container assembly of claim 5, wherein a lower portion of finger grip luer adapter is configured to be removably couplable to the elongate receptacle of the container lid.

8. The container assembly of claim 7, wherein the lower portion of the finger grip luer adapter comprises external threads, and wherein the external threads are configured to mate with a corresponding internal thread portion of the elongate receptacle.

9. The container assembly of claim 1, wherein the finger grip luer adapter is threadingly coupled to the container lid.

10. The container assembly of claim 9, wherein the finger grip luer adapter is removable from the container lid by way of counterclockwise rotation of the elongate cap when the elongate cap is coupled to the finger grip luer adapter.

11. The container assembly of claim 1, wherein at least one of the collection container and the container lid are formed of a polymeric resin.

12. The container assembly of claim 1, wherein the elongate cap is formed of a polymeric resin.

13. A container lid assembly for use with a container assembly for collecting a fluid specimen, the container lid comprising:

an elongate receptacle having an open end portion defined within the container lid and configured to receive a specimen collection tube therein;

a finger grip luer adapter removably coupled to the container lid within the elongate receptacle, the finger grip luer adapter comprising a needle extending therefrom; and an elongate cap removably coupled to the finger grip luer adapter and configured to extend over at least the needle of the finger grip luer adapter, wherein an upper portion of the elongate cap extends above at least a portion of the open end portion of the elongate receptacle when coupled to the finger grip luer adapter;

wherein the finger grip luer adapter is removable from the elongate receptacle through the open end portion of the elongate receptacle.

14. The container lid assembly of claim 13, wherein a distal end of the elongate cap is configured to slip-fittingly or press-fittingly couple to an upper portion of the finger grip luer adapter.

15. The container lid assembly of claim 14, wherein the upper portion of the finger grip luer adapter comprises a ribbed or textured surface.

16. The container lid assembly of claim 14, wherein a lower portion of finger grip luer adapter is configured to be removably couplable to the elongate receptacle of the container lid.

17. The container lid assembly of claim 16, wherein the lower portion of the finger grip luer adapter comprises external threads, and wherein the external threads are configured to mate with a corresponding internal thread portion of the elongate receptacle.

18. The container lid assembly of claim 17, wherein the finger grip luer adapter is removable from the container lid by way of counterclockwise rotation of the elongate cap when the elongate cap is coupled to the finger grip luer adapter.

19. A method of forming a container assembly for collecting a fluid specimen, the method comprising:

providing a collection container defining a chamber for receiving the fluid specimen;

providing a container lid couplable to the collection container, wherein the container lid comprises an elongate receptacle having an open end portion defined within the container lid and configured to receive a specimen collection tube therein;

coupling a finger grip luer adapter to the container lid within the elongate receptacle, the finger grip luer adapter comprising a needle extending therefrom; and coupling an elongate cap to the finger grip luer adapter such that the elongate cap extends over at least the needle of the finger grip luer adapter, wherein an upper portion of the elongate cap extends above at least a portion of the open end portion of the elongate receptacle when coupled to the finger grip luer adapter;

wherein the finger grip luer adapter is removable from the elongate receptacle through the open end portion of the elongate receptacle.

20. The method of claim 19, wherein the finger grip luer adapter is threadingly coupled to the elongate receptacle of the container lid.

* * * * *